US009655919B2

(12) United States Patent
Korzenik et al.

(10) Patent No.: US 9,655,919 B2
(45) Date of Patent: *May 23, 2017

(54) METHODS AND COMPOSITIONS FOR BOWEL CLEANSING BEFORE A MEDICAL PROCEDURE

(75) Inventors: Joshua Korzenik, Dover, MA (US); Corey A. Siegel, Hanover, NH (US); Douglas Knuth, Lebanon, NH (US)

(73) Assignee: The General Hospital Corporation, Boston, MA (US)

(*) Notice: Subject to any disclaimer, the term of this patent is extended or adjusted under 35 U.S.C. 154(b) by 1024 days.

This patent is subject to a terminal disclaimer.

(21) Appl. No.: 13/002,887

(22) PCT Filed: Jul. 9, 2009

(86) PCT No.: PCT/US2009/050167
§ 371 (c)(1),
(2), (4) Date: Aug. 10, 2011

(87) PCT Pub. No.: WO2010/006209
PCT Pub. Date: Jan. 14, 2010

(65) Prior Publication Data
US 2011/0288180 A1 Nov. 24, 2011

Related U.S. Application Data

(60) Provisional application No. 61/134,242, filed on Jul. 9, 2008.

(51) Int. Cl.
A61K 31/08 (2006.01)
A61K 31/765 (2006.01)
A23L 2/52 (2006.01)
A61K 9/00 (2006.01)
A23L 33/00 (2016.01)
A23L 33/10 (2016.01)

(52) U.S. Cl.
CPC .............. A61K 31/765 (2013.01); A23L 2/52 (2013.01); A23L 33/10 (2016.08); A23L 33/30 (2016.08); A23L 33/40 (2016.08); A61K 9/0056 (2013.01); A23V 2002/00 (2013.01)

(58) Field of Classification Search
None
See application file for complete search history.

(56) References Cited

U.S. PATENT DOCUMENTS

| 2,367,166 | A | 1/1945 | Balston |
| 6,866,873 | B2* | 3/2005 | Stern ............................ 424/725 |
| 2004/0009236 | A1* | 1/2004 | Halow ................. A61K 31/765 424/606 |
| 2007/0166411 | A1 | 7/2007 | Anthony et al. |
| 2010/0278949 | A1 | 11/2010 | Scott |

FOREIGN PATENT DOCUMENTS

| EP | 0423771 | 4/1991 |
| JP | 11 343251 | 12/1999 |
| JP | 2007-217398 | 8/2007 |
| WO | 02/30439 | 4/2002 |
| WO | WO 02/30439 | * 4/2002 |
| WO | 03/086172 | 10/2003 |
| WO | 2006/069422 | 7/2006 |
| WO | 2006/122104 | 11/2006 |
| WO | WO 2006/122104 | * 11/2006 |
| WO | 2007/083594 | 7/2007 |
| WO | 2010/006209 | 1/2010 |

OTHER PUBLICATIONS

McCray et al (Nutrition Issues in Gastroenterology, Series #56:41-57, 2007).*
Patent Examination Report No. 1 issued in Australian Application No. 2009268453 on Oct. 11, 2013 (4 pages).
Dahshan, "A randomized, prospective study to evaluate the efficacy and acceptance of three bowel preparations for colonoscopy in children," Am. J. Gastroenterol., 94(12):3497-501 (1999).
Delegge and Kaplan, "Efficacy of bowel preparation with the use of a prepackaged, low fibre diet with a low sodium, magnesium citrate cathartic vs. a clear liquid diet with a standard sodium phosphate cathartic," Aliment Pharmacol Ther, 21;1491-1495 (2005).
Hawes et al., "A consensus document on bowel preparation before colonoscopy: prepared by a task force from the American Society of Colon and Rectal Surgeons (ASCRS), the American Society for Gastrointestinal Endoscopy (ASGE), and the Society of American Gastrointestinal and Endoscopic Surgeons (SAGES).," Gastrointestinal Endoscopy, 63(7):894-909 (2006).
Communication pursuant to Article 94(3) EPC; Fischer, J. ; Feb. 5, 2013; European Patent Office (EPO); 09795214.7; 5 pages.
International Search Report and Written Opinion dated Feb. 9, 2010 issued in international application No. PCT/US2009/050167, 12 pgs.
Supplementary European Search Report issued in EP 09 79 5214 on Nov. 15, 2011.
Database WPI, Week 200841, Thomson Scientific, London, GB; AN 2008-G53654 (Jul. 26, 2007).
Office Action issued in CA2,736,183 on May 21, 2015 (4 pages).
Office Action issued in EP09795214.7 on Aug. 6, 2015 (4 pages).
European Office Action in European Application No. 09795214, dated Sep. 26, 2016, 3 pages.
Office Action in U.S. Appl. No. 15/085,363, dated Aug. 10, 2016, 14 pages.
Office Action issued in CA2,736,183 on May 21, 2015, 5 pages.
Office Action issued in Canadian Application No. 2,736,183 issued on Mar. 17, 2016, 6 pages.
Office Action issued in EP09795214.7 on Aug. 6, 2015, 4 pages.
Patent Examination Report No. 1 issued in Australian Application No. 2009268453 on Oct. 11, 2013, 5 pages.

(Continued)

Primary Examiner — Craig Ricci
(74) Attorney, Agent, or Firm — Fish & Richardson P.C.

(57) ABSTRACT

Described are kits, food compositions and methods for cleaning the bowel, e.g., in preparation for a medical procedure, e.g., a diagnostic or treatment procedure, such as an endoscopic or surgical procedure, or radiologic imaging such as CT colography.

18 Claims, 10 Drawing Sheets

(56) References Cited

OTHER PUBLICATIONS

Supplementary European Search Report issued in EP 09 79 5214 on Nov. 15, 2011, 2 pages.

\* cited by examiner

FIGURE 1A

Sample Instructions and Menu

To develop a complete preparation for your colonoscopy, please check the number of boxes requested under each category. Choose any combination of items below.

*Breakfast*
*Please check 1 box*
- ☐ Cream of wheat with milk/soymilk (4 ounces)
- ☐ Rice Krispies with milk/soymilk (4 ounces)
- ☐ Puffed rice with milk/soymilk (4 ounces)
- ☐ Sugar Smacks with milk/soymilk (4 ounces)
- ☐ Cocoa Krispies with milk/soymilk (4 ounces)
- ☐ Raspberry muffin
- ☐ English muffin with peach jelly
- ☐ Vanilla yogurt
- ☐ Pancakes with maple syrup
- ☐ Protein drinks (8 ounces)
- ☐ Yogurt smoothie

Snacks
*Please check 3 boxes*
- ☐ Freezer pops
- ☐ Jell-O with Cool Whip (lemon, lime, orange)
- ☐ Vanilla yogurt with fruit syrup
- ☐ Protein drink (counts as 1 beverage serving)
- ☐ Cottage cheese with fruit syrup
- ☐ Yogurt smoothie
- ☐ Pretzels

Lunch/Dinner
*Please check 2 boxes*
- ☐ Bowties with creamy roasted red pepper sauces (lunch only)
- ☐ Linguine with garlic sauce
- ☐ Cheese ravioli with Alfredo sauce
- ☐ Spicy tofu
- ☐ Herb baked cod
- ☐ Oriental rice bowel
- ☐ Ramen noodles
- ☐ Maple glazed sweet potatoes
- ☐ Garlic mashed potatoes
- ☐ Zesty vegetable consommé (counts as 1 beverage serving)
- ☐ Creamy chicken soup

FIGURE 1B

Desserts
*Please check 2 boxes*
- ☐ Raspberry cream
- ☐ Angel food cake with fruit syrup
- ☐ Lemon dessert
- ☐ Baked custard/flan
- ☐ Butterscotch pudding
- ☐ Coconut pudding
- ☐ Almond pudding
- ☐ Sugar wafers
- ☐ Vanilla wafers

Beverages
*Please select a total of TWELVE drinks (2 drinks for each meal and all 3 snacks.*

| | | | | |
|---|---|---|---|---|
| Pineapple juice | 0 | 1 | 2 | 3 |
| White cranberry juice | 0 | 1 | 2 | 3 |
| White grape juice | 0 | 1 | 2 | 3 |
| Apple juice | 0 | 1 | 2 | 3 |
| Lemonade | 0 | 1 | 2 | 3 |
| Limeade | 0 | 1 | 2 | 3 |
| White grapefruit juice | 0 | 1 | 2 | 3 |
| White cranpeach juice | 0 | 1 | 2 | 3 |
| White ice tea | 0 | 1 | 2 | 3 |
| Coffee (limit to 1 cup at breakfast) | 0 | 1 | | |
| Tea (limit to 1 cup at breakfast) | 0 | 1 | | |
| White teas | 0 | 1 | 2 | 3 |
| Chai | 0 | 1 | 2 | 3 |
| Broth (beef, chicken, vegetable) | 0 | 1 | 2 | 3 |
| Soda (Fresca, Sprite, Ginger Ale) | 0 | 1 | 2 | 3 |

FIGURE 2A

Regular Diet

*Breakfast*
- English muffin with peach jelly
- Yogurt smoothie
- White grapefruit juice
- Coffee(1 at breakfast)

*Morning Snack*
- Pretzels with mustard
- White ice tea

*Lunch*
- Bowties with creamy red pepper sauce(lunch)
- Maple glazed sweet potatoes(lunch)
- Soda(grapefruit, lemon-lime, ginger ale)
- Raspberry cream

*Afternoon Snack*
- Protein drink
- White cran-peach juice

*Dinner*
- Oriental rice bowl
- Butterscotch pudding
- Lemonade

*Bedtime Snack*
- Gelatin with non-dairy topping
- Apple juice

*Breakfast*
- Broth(beef, chicken, vegetable
- Apple juice
- Gelatin

FIGURE 2B

Pediatric Diet

*Breakfast*
- Cocoa rice cereal with milk/soymilk (4 ounces)
- Yogurt smoothie(4 ounces)
- White grape juice

*Morning Snack*
- Freezer pops
- Soda(grapefruit, lemon-lime, ginger ale)

*Lunch*
- Sugar coated rice with milk/soymilk (4 ounces)
- Butterscotch pudding
- Lemonade

*Afternoon Snack*
- Freezer pops
- Yogurt smoothie

*Dinner*
- Thin oriental noodles
- Vanilla yogurt with fruit syrup
- White grape juice

*Bedtime Snack*
- Gelatin with non-dairy topping
- Apple juice

*Breakfast*
- Broth (beef, chicken, vegetable)
- Apple juice
- Gelatin

FIGURE 2C

Diabetic Diet

*Breakfast*
    Raspberry muffin
    Puffed rice with milk/soymilk(4 ounces)
    White cranberry juice
    Coffee (4 ounces)

*Morning Snack*
    Diet gelatin with non-dairy topping
    Vanilla wafers
    Diet soda (grapefruit, lemon-lime, ginger ale)

*Lunch*
    Herb Bake Cod
    Angel food cake with fruit sauce
    Sugar free lemonade

*Afternoon Snack*
    Diabetic protein drink
    Angel food cake with fruit sauce

*Dinner*
    Linguine with garlic sauce
    Sugar free lemonade
    Lemon dessert

*Bedtime Snack*
    Diet gelatin with non-dairy topping
    Sugar free lemonade

*Breakfast*
    White cranberry juice
    Diet gelatin
    Broth (beef, chicken, vegetable)

FIGURE 2D

Renal Diet

*Breakfast*
- Raspberry muffin
- Puffed rice with milk/soymilk(4 ounces)
- White cranberry juice
- Coffee (4 ounces)

*Morning Snack*
- Gelatin with non-dairy topping
- Vanilla wafers
- Soda(grapefruit, lemon-lime, ginger ale)

*Lunch*
- Herb Bake Cod
- Sugar wafers
- Sugar free lemonade

*Afternoon Snack*
- Renal protein drink
- Angel food cake with fruit sauce

*Dinner*
- Linguine with garlic sauce
- Sugar free lemonade
- Lemon dessert

*Bedtime Snack*
- Gelatin with non-dairy topping
- Sugar free lemonade

*Breakfast*
- White cranberry juice
- Gelatin

FIGURE 3A

| Breakfast | Regular | Diabetic | Renal | Liver | Pediatric | Gluten Free | Vegetarian | Kosher |
|---|---|---|---|---|---|---|---|---|
| Yogurt smoothie | X | X | | X | X | | X | X |
| Protein drinks (8 ounces) | X | X | X | | X | X | X | X |
| Pancakes with maple syrup | X | | | X | X | X | | X |
| Vanilla yogurt | X | X | X | X | X | | X | X |
| English muffin with peach jelly | X | | X | X | X | | X | X |
| Raspberry muffin | X | | X | X | X | | | X |
| Cocoa rice cereal with milk/soymilk (4 ounces) | X | X | X | X | X | X | X | X |
| Sugar coated rice with milk/soymilk (4 ounces) | X | | X | X | X | X | X | X |
| (4 ounces) Puffed rice with milk/soymilk | X | X | X | X | X | X | X | X |
| Rice Krispies with milk/soymilk (4 ounces) | X | X | X | X | X | X | X | X |
| Cream of wheat/rice with milk/soymilk (4 ounces) | X | X | X | X | X | X | X | X |

FIGURE 3B

| Snacks | Regular | Diabetic | Renal | Liver | Pediatric | Gluten Free | Vegetarian | Kosher |
|---|---|---|---|---|---|---|---|---|
| Freezer pops | X | | X | X | X | X | X | X |
| Gelatin with non-dairy topping | X | X | X | X | X | X | X | X |
| Vanilla yogurt with fruit syrup | X | X | X | X | X | | X | X |
| Protein drink | X | X | X | X | X | X | X | X |
| Cottage cheese with fruit syrup | X | X | X | X | X | X | X | X |
| Yogurt smoothie | X | X | X | X | X | X | X | X |
| Pretzels with mustard | X | X | | | X | | X | X |

FIGURE 3C

| Lunch/Dinner | Regular | Diabetic | Renal | Liver | Pediatric | Gluten Free | Vegetarian | Kosher |
|---|---|---|---|---|---|---|---|---|
| Bowties with creamy red pepper sauce (lunch) | X | X | X | X | X | | X | X |
| Linguine with garlic sauce | X | X | X | X | X | | X | X |
| Spicy tofu | X | X | X | X | X | X | X | X |
| Herb Bake Cod | X | X | X | X | X | X | | X |
| Oriental rice bowl | X | X | | | X | | X | X |
| Thin Chinese noodles | X | X | | | X | | X | X |
| Maple glazed sweet potatoes (lunch) | X | X | | | X | X | X | X |
| Garlic mashed potatoes | X | X | | | X | X | X | X |
| Zesty vegetable consommé | X | X | | | X | | X | X |

FIGURE 3D

| Beverages | Regular | Diabetic | Renal | Liver | Pediatric | Gluten Free | Vegetarian | Kosher |
|---|---|---|---|---|---|---|---|---|
| Pineapple juice | X | X | X | X | X | X | X | X |
| White cranberry juice | X | X | X | X | X | X | X | X |
| White grape juice | X | X | X | X | X | X | X | X |
| Apple juice | X | X | X | X | X | X | X | X |
| Lemonade | X | X | X | X | X | X | X | X |
| Limeade | X | X | X | X | X | X | X | X |
| White grapefruit juice | X | X | X | X | X | X | X | X |
| White cran-peach juice | X | X | X | X | X | X | X | X |
| White ice tea | X | X | X | X | X | X | X | X |
| Coffee (1 at breakfast) | X | X | X | X | | X | X | X |
| Tea (1 at breakfast) | X | X | X | X | | X | X | X |
| White tea | X | X | X | X | X | X | X | X |
| Chai | X | X | X | X | X | | X | X |
| Broth (beef, chicken, vegetable) | X | X | | | X | | X | X |
| Soda (grapefruit, lemon-lime, ginger ale) | X | X | X | X | X | X | X | X |
| Sugar free lemonade | x | x | x | x | x | x | x | x |

METHODS AND COMPOSITIONS FOR BOWEL CLEANSING BEFORE A MEDICAL PROCEDURE

CLAIM OF PRIORITY

This application is a 371 application of PCT/US2009/050167, filed on Jul. 9, 2009, and claims the benefit of U.S. Provisional Patent Application Ser. No. 61/134,242, filed on Jul. 9, 2008, the entire contents of which are hereby incorporated by reference.

TECHNICAL FIELD

This invention relates to kits, food compositions and methods for cleaning the bowel, e.g., in preparation for a medical procedure, e.g., a diagnostic or treatment procedure, such as an endoscopic or surgical procedure, or radiologic imaging such as CT colography.

BACKGROUND

An estimated six million colonoscopies are performed annually in the United States, predominantly as a screening procedure to prevent colon cancer. Many patients report the most difficult aspect of the procedure is the preparation taken the day, night and morning before the procedure to evacuate stool and any other residue from the colon to allow for optimal visualization of the colon during the colonoscopic examination. The several existing options for cleaning the colon involve a variety of means providing a large amount of fluid (i.e., whole bowel irrigation), both orally ingested as well as induced through secretions of the small bowel, to wash out bowel contents.

A widely used whole bowel irrigation liquid formulation includes polyethelene glycol (PEG) in solution with electrolytes. These are non-absorbed solutions that require the ingestion of a substantial amount of fluid. These PEG lavage preparations (e.g., GOLYTELY, NULYTELY, and HALF-LYTELY from Braintree Laboratories Inc. (Braintree, Mass.), and the fruit flavored COLYTE from Schwarz Pharma, Inc. (Mequon, Wis.), which are usually taken by the patient at home the night or evening before the examination, cleanse the bowel through the induction of diarrhea. The osmotic activity of polyethylene glycol, in combination with the electrolyte concentration, results in virtually no net absorption or excretion of ions or water. Accordingly, large volumes can be administered without significant changes in fluid and electrolyte balance. Individuals undergoing these whole bowel irrigation preparations complain of nausea and often vomiting because of the need to take in a large amount of (unpleasant) tasting fluid and significant hunger. While most patients understand the need to clear the bowel completely prior to an endoscopic procedure—adequate preparation is key to an accurate colonoscopy—many balk at these unpleasant whole bowel irrigation preps.

SUMMARY

Described herein are a variety of prepared, low residue foods that contain a variety of laxatives as ingredients and incorporate an adequate amount of fluid so that an individual undergoing this preparation can continue to take in nutrition (unlike existing preps) while preparing for a procedure. In general, a large amount of distasteful fluid (whole bowel irrigation) would not be required. Different foods including appetizers, soups, main courses, desserts, snacks, and beverages are prepared with a variety of laxatives incorporated therein as ingredients so that the food itself is the delivery vehicle for the bowel cleanse. The food includes a variety of low residue foods, and can include foods with increasingly less residue as those taken closer to the procedure.

Thus, in one aspect, the invention provides kits for providing a therapeutic dietary regimen including a plurality of therapeutic foods for the preparation of a subject's bowel for a medical procedure. In general, the kits include enough food items for all of the meals to be ingested by the subject for a specified period prior to the medical procedure (e.g., the 24 hours before, the 48 hours before, the day before, or the day before and morning of, e.g., from 48 or 24 hours up to 2, 3, 4, 5, or 6 hours before). In some embodiments, the food items are low fiber, low residue foods, and some or all of the food items have incorporated therein an amount of a laxative agent sufficient to induce in the subject the production of watery yellow stools with a light yellow effluent. The kits and foods described herein are intended for use, and are effective for preparing the bowel, without the use of whole bowel irrigation.

In some embodiments, the kits also include all of the beverages to be consumed by the subject during the specified period. In some embodiments, the volume of all of the liquid foods and beverages to be consumed by the subject during the preparation period is less than about 2.5 liters, or less than 2 liters.

In some embodiments, the foods in the kit include a total of 0-6 g fiber. In some embodiments, the foods in the kit further include a total of 0.3-15 g Total Fats; 0-150 mg Cholesterol; 100-500 g of carbohydrates and 10-80 g of protein.

In some embodiments, the kits include solid foods (e.g., pasta, cookies, or bars) and liquid foods (e.g., soups, smoothies, and beverages).

In some embodiments, the medical procedure is selected from the group consisting of colonoscopy, intestinal surgery, virtual colography, and barium studies.

In another aspect, the invention provides methods for preparing a subject's bowel for a medical procedure, e.g., for assisting a subject in preparing their bowel, the method including providing to (e.g., administering to, or prescribing for, or providing instructions regarding) the subject a therapeutic dietary regimen including a plurality of therapeutic foods, i.e., a dietary regimen that includes all the meals that are to be ingested by the subject for a specified period prior to the medical procedure (e.g., the 24 hours before, the 48 hours before, the day before, or the day before and morning of, e.g., from 48 or 24 hours up to 2, 3, 4, 5, or 6 hours before). In some embodiments, the food items are low fiber, low residue foods, and some or all of the food items have incorporated therein an amount of a laxative agent sufficient to induce in the subject the production of watery yellow stools with a light yellow effluent. The methods described herein are intended for use, and are effective for preparing the bowel, without the use of whole bowel irrigation.

In some embodiments, all of the beverages to be consumed by the subject during the specified period are also provided or specified, and some or all of the beverages also include a laxative agent. In some embodiments, the volume of all of the liquid foods and beverages to be consumed by the subject during the preparation period is less than about 2.5 liters, or less than 2 liters.

In some embodiments, the foods (and optionally beverages) include a total of 0-6 g fiber. In some embodiments, the foods (and optionally beverages) further include a total of 0.3-15 g Total Fats; 0-150 mg Cholesterol; 100-500 g of carbohydrates and 10-80 g of protein.

In some embodiments, the methods include providing solid foods and liquid foods.

In some embodiments, the methods include administering very low- or no-residue foods to be consumed up to two hours prior to the procedure, e.g., to be consumed between 6 (e.g., 12, 11, 10, 9, 8, 7) hours and 2 hours before the procedure.

Also described herein is the use of the kits and foods described herein in a method (described herein) of preparing a subject's bowel for a medical procedure.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-B show a sample selectable menu and instructions for use.

FIGS. 2A-2D show exemplary menus for subjects on normal diets (2A), pediatric diets (2B), diabetic diets (2C), and renal diets (2D).

FIGS. 3A-3D show restrictions on the food types for subjects with special diets, e.g., pediatric, diabetic, liver (i.e., for subjects with compromised liver function), gluten free, vegetarian, Kosher and renal (i.e., for subjects with compromised kidney function) diets. X indicates a food that is available for selection for that category of subject.

DETAILED DESCRIPTION

Millions of Americans undergo bowel preparations annually, to prepare for colonoscopies, intestinal surgery (e.g., polypectomy, resection, colostomy, or ileostomy), virtual colography, and barium studies (e.g., using a barium enema). These preps are usually performed using a liquid preparation for whole bowel irrigation; although phospha soda formulations in pill form are available, their use has been restricted due to possible renal injury.

Current recommendations for an appropriate diet before colonoscopy restrict diet to clear liquids and/or a low residue foods for 1-4 days prior to initiating the bowel cleansing product (see Hawes et al., Gastrointestinal Endoscopy 63 (7):894-909 (2006)). Current preparation regimes indicate that any intake of solids or liquids other than what is part of the prep must be stopped prior to initiating the prep. For example, one commercially-available diet, NUTRA-PREP™ (E-Z-EM, Lake Success, N.Y.), formalizes some of these practices in a prepackaged set of meals to be taken prior to beginning a prep. As described in U.S. Pat. No. 6,866,873 (with which the NUTRA-PREP is marked), clinical tests (see, e.g., Delegge and Kaplan, Aliment Pharmacol Ther 21:1491-1495 (2005)), and the patient instructions, the NUTRA-PREP diet is to be taken prior to initiating any of the bowel prep products with a minimum specified time interval between completing the final intake of food and beginning the bowel cleansing product. U.S. Pat. No. 6,866, 873 teaches that the meals are to be utilized prior to the use of any bowel cleansing products, which are to then used as indicated. While these bowel cleansing products differ in content and amount of water to be taken along with them, the instructions for each prep is to complete intake of food or liquids (other than the water which is part of some preps) prior to initiating the product. As described in Delegge and Kaplan, Aliment Pharmacol Ther 21:1491-1495 (2005), patients in a clinical study of the effectiveness of the NUTRA-PREP regime consumed the NUTRA-PREP food prior to initiation of the LOSO prep, which was begun at 4 PM the day before the colonoscopy, thus requiring a fast of longer than 12 hours for most patients.

In contrast, the methods and composition described herein differ from existing preps (including NUTRA-PREP), at least in that food is used as the delivery vehicle for the prep, so that an individual continues dietary intake, e.g., provided in a prepared diet, in order to deliver the bowel cleansing product efficiently and effectively to perform the prep. This concept runs contrary to existing art, established practice and expert opinion of how a colon can be prepared for a colonoscopy, gastrointestinal surgery or virtual (CT) colography. By utilizing food to deliver the prep, the present methods are contradictory in theory and practice to currently accepted methods, which as noted above require that the individual cease taking in food or liquids (other than those required by the prep) in order to sufficiently cleanse the colon. The methods described herein provide an adequate cleansing and do not require that dietary intake be discontinued prior to initiating a prep, and therefore do not require a prolonged fast; this will encourage and assist with complete ingestion of the prep (as many patients have difficulty with existing preps due to unpalatable taste, "taste fatigue," and side effects like nausea and fasting) and will enhance the cleansing of the colon. As most patients find the most difficult part of the colonoscopy experience is the prep and not the procedure itself, the approach described herein will improve the quality of the experience significantly by enhancing acceptability of the prep, decreasing side effects (dizziness, dehydration, nausea, vomiting, taste fatigue, etc) and thereby provide a better prep for the colon. This approach may also reduce healthcare costs by increasing the percentage of adequately prepped colons and reducing the wasted resources related to the need to cancel and repeat colonoscopies for inadequately prepped patients.

Thus, described herein are therapeutic food compositions that include low-residue foods with cleansing agents incorporated therein, for use in the preparation of the bowel for procedures including colonoscopy, intestinal surgery, virtual colography, and barium studies (barium enema), inter alia, and methods of use thereof.

Low-Residue Foods

As used herein, the term "food" or "foods" includes both solid and liquid forms of food, including beverages. As used herein, a low residue diet typically contains less than about 5 or 6 grams of fiber per day, and generally limits foods that leave significant amounts of fecal residue in the colon. Low residue foods are those that leave little or no residue in the bowel, and can include white bread, refined pasta and cereals, and white rice; some canned or well-cooked fruits or vegetables that do not include skins, peels or seeds; tender, ground, and well cooked meat, fish, eggs, and poultry; less than 2 cups per day of milk and yogurt; mild cheeses, such as ricotta and cottage cheese; butter, mayonnaise, vegetable oils, margarine, plain gravies and dressings; broth and strained soups from allowed foods; and pulp free, strained, or clear juices. In some embodiments, the foods useful in the methods and compositions described herein should:

1. Omit raw, high fiber vegetables and fruits
2. Omit whole grains, seeds, nuts and skins
3. Omit high fats foods that slow gastric emptying
4. Fiber content per serving should be 1 gram or less, for a total of less than about 5 or 6 grams per day
5. Dairy intake is limited to 2 cups per day, including puddings and strained cream soups.

Table 1 provides an exemplary listing of foods allowed and excluded from a low fiber/low residue diet. One of skill in the art will readily be able to identify other foods that can be used, and those that should be avoided.

TABLE 1

Low Fiber/Residue Diet

| Food Group | Allowed | Excluded |
|---|---|---|
| Starch | Cereals, rice, pasta, and other products made with refined grains | Whole grain cereals, rice, pasta, legumes, and popcorn |
| Vegetables | Strained vegetable juices, Potatoes without skins | All vegetables |
| Fruits | Fruit juices except prune | All fruits including canned |
| Dairy | Limited to 2 cups per day including yogurts, smoothies, puddings and strained cream soups | Whole milk/cream or foods made with them; cheese |
| Meats/Meat Substitutes | Eggs, fish, (tofu) | Beef, pork, chicken, processed meats, dried peas/beans, peanut butter |
| Desserts | Gelatin, pudding, sherbet, sorbet, custards, plain cake (angel food), plain cookies (sugar), yogurt, smoothies | All pastries plus desserts that contain skins, nuts, seeds and raisins |
| Beverages | Coffee and tea (limited), non-cola sodas, pulp free fruit juices, pulp free fruit ice white ice tea, non-caloric teas and beverages, freezer pops, milk (limited intake), smoothies, protein drinks | |
| Miscellaneous | | Nuts, seeds |

In addition, the foods useful in the kits, compositions and methods described herein are low in fat (i.e., less than 15 grams of fat per day or prep period) and bland colored (e.g., white, cream, yellow, or clear) to allow for adequate colon cleansing.

The general nutritional value of a 24 hour regimen of the foods described herein is set forth in Table 2.

TABLE 2

Nutritional Value

| Calories | 1000-2500 |
|---|---|
| From Carbohydrate | 400-2000 |
| From Fat | 5-200 |
| From Protein | 80-320 |
| Total Carbohydrate | 100-500 g |
| Dietary Fiber | 0-6 g |
| Protein | 10-80 g |
| Total Fats | 0.3-15 g |
| Cholesterol | 0-150 mg |

The foods can be in forms that include, but are not limited to, soups (broths, chicken noodle soup), juices, teas, milk, pancakes with syrup, low-fat muffins, yogurt smoothies, pasta with sauce, puddings, and custards. A number of sample recipes are provided herein, see below.

FIGS. 2A-3D show exemplary (non-limiting) menus for subjects on normal diets (2A), pediatric diets (2B), diabetic diets (2C), and renal diets (2D). FIGS. 3A-3D show exemplary (non-limiting) food restrictions for subjects with special diets, e.g., pediatric, diabetic, liver (i.e., for subjects with compromised liver function), gluten free, vegetarian, Kosher and renal (i.e., for subjects with compromised kidney function) diets.

Laxative Agents

Rather than relying on one agent as is done at present in essentially all existing preparations, the present methods can utilize a variety of agents including, but not limited to, hydrating agents (osmotics), e.g., dibasic sodium phosphate, magnesium citrate, magnesium hydroxide (milk of magnesia), magnesium sulfate (Epsom salt), monobasic sodium phosphate, sodium biphosphate, lactulose, polyethylene glycol (PEG), e.g., PEG 3350, vitamin C, and sorbitol. Other laxative agents are known in the art, e.g., those described in Delegge and Kaplan, Aliment Pharmacol Ther 21:1491-1495 (2005).

In some embodiments, the laxative agent is not a senna laxative, e.g., is not an anthraquinone derivative (e.g., not a glycoside or sennoside).

The dose of the laxative provided in each meal should be an amount sufficient to induce the presence of watery yellow stools with light yellow or clear effluent within about 6-8 hours of the initiation of the prep; this effluent is a clinical indicator of an adequate cleansing of the colon and is used as a clinical guide and surrogate marker for an adequate colon cleansing to permit a thorough inspection of the lining of the colon.

Exemplary doses of the laxative agents are as follows:

| magnesium citrate | 0-20 oz |
|---|---|
| PEG 3350 | 0-255 gms |
| milk of magnesia | 0-120 ml |
| magnesium sulfate | 0-2 tablespoons |
| lactulose | 0-120 ml (0-90 gms) |
| vitamin C | 0-40 gms |
| sorbitol | 0-100 ml of 70% solution |

Since combinations of the agents can be used, one of skill in the art will be able to determine an appropriate dose. In one example, if only PEG 3350 is used, a dose of about 255 g per day can be used; if only sorbitol is used, about 100 ml per day of a 70% solution can be used. As a further example, if a combination of the two is used, e.g., 50% PEG 3350 and 50% sorbitol, then the doses given above can be altered correspondingly.

Methods of Preparation

The foods described herein can be made using standard cooking methods known in the art, including processing, mixing, precooking, cooking (including baking, steaming, and frying, inter alia), freezing, dehydrating or freeze-drying. The laxative agents can be incorporated therein by any method including mixing in as an ingredient e.g., as in a baked good, or by inclusion as a topping, sauce, or glaze, e.g., as in a sauce for pasta or a protein source such as meat or tofu.

In some embodiments, a kit is provided that includes all of the meals required for a subject to complete the preparation for the procedure, e.g., all of the meals that the subject will consume the day before the procedure. In some embodiments, the kit also include all of the beverages that the subject will consume. The kit can also include instructions for use in a method described herein.

In some embodiments, the foods are provided in prepackaged form, e.g., packed in a container, e.g., in a shelf stable, refrigerated, or frozen form. The kits can be purchased, e.g., from a pharmacy or other retail outlet.

Additionally, the food can be prepared and packaged such that some or all of the food items require some (preferably simple) preparation by the subject, e.g., mixing (e.g., by hand or in a blender or food processor), cooking (e.g., on a stove top, in an oven or microwave), or diluting, e.g., by adding cool, hot or boiling water, or by submerging the food item into boiling water. Alternatively, some or all of the foods can be provided to the subject in ready-to-eat form, e.g., as a bar or canned liquid (e.g., a beverage).

In some embodiments, the foods are prepared to order once the subject has made menu selections. The foods can be prepared, e.g., by a health care institution such as a clinic or inpatient facility, or by a specialized producer of such foods. The foods can then be delivered to the subject, e.g., at home or in a facility, or picked up by the patient.

Methods of Use

The foods described herein are intended for consumption by subjects preceding a procedure that requires a clean bowel, i.e., a medical procedure such as a surgical or diagnostic procedure, to prepare the bowel for the procedure. Such procedures include colonoscopy, intestinal surgery, virtual colography, fiberoptic endoscopy, sigmoidoscopy, wireless capsule endoscopy (WCE) (which uses a miniaturized scope administered in a "pill" form) and barium studies (barium enema), inter alia.

In some embodiments, patients are given a menu from which they can make a certain number of choices among several different groups of foods in order to take in adequate amounts of laxatives and fluid to provide an adequate bowel preparation (see an example menu set forth in FIGS. 1A-1B). These instructions can be provided directly by their health care provider, or can be provided to the patient, e.g., via a pamphlet, package insert or internet web page. Once selections are made, the foods can be, e.g., obtained from a supplier, or delivered to the patient's home for consumption.

In some embodiments, the methods of treatment will include the ingestion of these foods starting at 72, 48, 36, 24, or 12 hours prior to a scheduled procedure; these foods can be consumed up to a few hours prior to the procedure, e.g., up to about 2, 3, 4, 5, or 6 hours prior to the procedure. The administration regimen can include the ingestion of foods with increasingly less residue closer to the procedure. For example, the meals consumed closer to the procedure can contain substantially no fiber (i.e., less than 1 g fiber) and no dairy products.

In general, the methods described herein do not include the use of a high-volume liquid prep as is known in the art (described above) for whole bowel irrigation. An enema, e.g., a tap water enema, may be used in some cases.

Sample Recipes

Although the following recipes specify MIRALAX™ (PEG 3350) or sorbitol, one of skill in the art will appreciate that equally effective amounts of other laxatives can also be used.

Raspberry Yogurt Muffins
23 grams of flour
5.5 grams sugar
0.4 grams baking soda
100 micrograms salt
5 milliliters orange juice
2.5 milliliters vegetable oil
0.2 milliliters almost extract
20 milliliters nonfat vanilla yogurt
4 grams liquid egg substitute
1 milliliter raspberry extract
17 grams MIRALAX
Directions:
Line a muffin tin with paper liners
Preheat oven to 400° F.
In large bowl combine flour, sugar, baking powder, baking soda, salt and MIRALAX.
Mix well.
In another bowl, whisk together orange juice, oil extracts, yogurt and egg. Add to dry ingredients and stir until moistened. Spoon into muffin liners.
Bake at 400 F for 20 minutes.

Yogurt Smoothie (orange-banana)
240 milliliters pulp free orange juice
240 milliliters of non-fat yogurt
0.5 grams of cinnamon
118 grams of ripe banana (1 medium)
17 grams MIRALAX
Directions:
Place all ingredients into blender, process until smooth.

Orange-Pineapple Popsicle
60 milliliters pulp free orange juice
60 milliliters pineapple juice
17 grams MIRALAX
Directions:
Mix and freeze in a popsicle mold.

Coconut Pudding 1
120 milliliters coconut milk
12.5 grams of sugar
8 grams of cornstarch
100 micrograms of salt
0.5 grams of cinnamon
17 grams MIRALAX
Directions:
In a saucepan, mix together cornstarch, salt, sugar, and MIRALAX. Whisk in coconut milk and simmer over medium heat. Stir constantly until mixture thickens. Pour into serving dishes and chill at least 1 hour. Optionally, garnish with cinnamon powder.

Coconut Pudding 2
236 grams coconut milk
28 grams of arrowroot
up to 30 ml of 70% sorbitol solution
Prepare as directed above for Coconut Pudding 1.

Cream of Rice Cereal
244 grams of cereal cooked with water without salt
112 gram of skim milk
up to 30 ml of 70% sorbitol solution
Mix cereal, rice and sorbitol together with water; heat and serve

EXAMPLE

The invention is further described in the following example, which does not limit the scope of the invention described in the claims.

Example 1

A pilot test was conducted with three subjects. Patients 1, 2 and 3 consumed the contents of a full menu designed for colon preparation. Items included in the menu are listed in Table 3. Results were uniform across all three subjects. Within 2-3 hrs of the beginning of the preparation all subjects had an urgency to move their bowels. Within 4-5 hours of beginning the preparation the subjects had a significant volume of watery diarrhea. By 6 hours after initiation of the preparation, the subjects all had watery yellow stools with an effluent appearance similar to what we expect at the time of colonoscopy. This light yellow effluent is a clinical indicator of an adequate cleansing of the colon and is used as a clinical guide and surrogate marker for an adequate colon cleansing to permit a thorough inspection of the lining of the colon.

Other than the diarrhea, effects included gas and mild abdominal cramping. No other side-effects were noted. All subjects noted that the food was good tasting, they were not hungry during the preparation, they did not experience taste fatigue, nausea or significant abdominal bloating.

TABLE 3

| Study Meals | | | | |
| --- | --- | --- | --- | --- |
| Breakfast | Snacks | Lunch | Dinner | Drinks |
| Pancakes w/ syrup | Fruit smoothie | Potato leek soup | Asian noodles | Apple juice |
| Blueberry muffin | Vanilla Pudding | Asian noodles | Frozen pop | Lemonade |
| Toasted rice cereal with soy milk | Pretzels with honey mustard | Creamy garlic sauce with noodles | Vegetable soup | Raspberry iced tea |
| SMOOTH MOVE$^R$ senna leaf tea (Traditional Medicinals, Sebastopol, CA) | Frozen pop | Tortellini with alfredo sauce | Fruit smoothie | White cranberry juice |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a subject for a colonoscopy, the method comprising providing to a subject in need thereof a plurality of food items to be ingested by the subject between 24 hours and 14 hours immediately prior to the colonoscopy,
    wherein said food items comprise low fiber solid and liquid foods having incorporated therein an amount of a laxative agent comprising polyethylene glycol sufficient to induce in the subject the production of watery yellow stools with a light yellow effluent,
    wherein said food items are prepared by mixing at least one food ingredient with polyethylene glycol, and wherein said food items comprise a shelf stable mixture of said at least one food ingredient and said polyethylene glycol.

2. The method of claim 1, further comprising providing all beverages to be ingested by the subject during the 24 hours prior to the medical procedure, and wherein at least one of the beverages to be ingested by the subject during the 24 hours prior to the medical procedure comprises a laxative agent.

3. The method of claim 1, wherein the plurality of food items that are provided comprise all of the foods to be ingested by the subject during the 24 hours prior to the medical procedure.

4. The method of claim 3, wherein each of the food items comprises a total of 0-6 g fiber.

5. The method of claim 4, wherein each of the food items further comprises a total of 0.3-15 g Total Fats; 0-150 mg Cholesterol; 100-500 g of carbohydrates and 10-80 g of protein.

6. The method of claim 1, wherein the medical procedure is selected from the group consisting of colonoscopy, intestinal surgery, virtual colography, and barium studies.

7. The method of claim 1, wherein the polyethylene glycol is PEG 3350.

8. The method of claim 2, wherein all the beverages to be ingested by the subject during the 24 hours prior to the medical procedure have a total volume that is less than 2.5 liters.

9. The method of claim 2, wherein all the beverages to be ingested by the subject during the 24 hours prior to the medical procedure have a total volume that is less than 2 liters.

10. The method of claim 1, wherein the method does not include whole bowel irrigation.

11. The method of claim 1, wherein the food items comprise at least one liquid food item.

12. The method of claim 11, wherein the at least one liquid food item is a smoothie.

13. The method of claim 11, wherein no laxative agent other than the laxative agent mixed with food items is provided to the subject for ingestion prior to the procedure.

14. The method of claim 1, wherein the food items provide a delivery vehicle for the laxative agent.

15. The method of claim 1, wherein the method eliminates or reduces side effects associated with administering to the subject food and laxative separately.

16. The method of claim 1, wherein the side effects comprise one or more of dizziness, dehydration, nausea, vomiting, and taste fatigue.

17. The method of claim 1, wherein the at least one laxative is provided in an amount sufficient to induce the presence of watery yellow stools with light yellow or clear effluent within about 6-8 hours after ingestion of the at least one food item by the subject.

18. The method of claim 1, wherein the plurality of food items provide calories to the subject when ingested.

* * * * *